(12) United States Patent
Nonaka

(10) Patent No.: US 9,636,037 B2
(45) Date of Patent: May 2, 2017

(54) ELECTRICAL IMPEDANCE MEASURING APPARATUS

(71) Applicant: NIHON KOHDEN CORPORATION, Tokyo (JP)

(72) Inventor: Yukio Nonaka, Tokyo (JP)

(73) Assignee: NIHON KOHDEN CORPORATION, Tokyo (JP)

(*) Notice: Subject to any disclaimer, the term of this patent is extended or adjusted under 35 U.S.C. 154(b) by 155 days.

(21) Appl. No.: 14/624,139

(22) Filed: Feb. 17, 2015

(65) Prior Publication Data

US 2015/0238115 A1  Aug. 27, 2015

(30) Foreign Application Priority Data

Feb. 27, 2014 (JP) ................................. 2014-037525

(51) Int. Cl.
*A61B 5/00* (2006.01)
*A61B 5/053* (2006.01)
*A61B 5/08* (2006.01)

(52) U.S. Cl.
CPC .............. *A61B 5/0536* (2013.01); *A61B 5/08* (2013.01); *A61B 5/6823* (2013.01); *A61B 5/742* (2013.01); *A61B 5/743* (2013.01); *A61B 5/7275* (2013.01)

(58) Field of Classification Search
CPC ..... A61B 5/053; A61B 5/0531; A61B 5/0535; A61B 5/0536; A61B 5/6823; A61B 5/742; A61B 5/743; A61B 5/08; A61B 5/7275

See application file for complete search history.

(56) References Cited

U.S. PATENT DOCUMENTS

| | | | |
|---|---|---|---|
| 8,321,007 B2 | 11/2012 | Teschner et al. | |
| 9,215,989 B2* | 12/2015 | Kaib | A61B 5/0006 |
| 9,370,312 B2* | 6/2016 | Schwartz | A61B 5/04085 |
| 9,384,549 B2* | 7/2016 | Leonhardt | G06T 7/0016 |
| 2010/0228143 A1 | 9/2010 | Teschner et al. | |

FOREIGN PATENT DOCUMENTS

JP  2012-061057 A  3/2012

OTHER PUBLICATIONS

Search Report from European Patent App. No. 15155679.2 (May 13, 2015).

(Continued)

*Primary Examiner* — Max Hindenburg
(74) *Attorney, Agent, or Firm* — Pearne & Gordon LLP

(57) ABSTRACT

An electrical impedance measuring apparatus includes: a plurality of electrodes adhered to a periphery of a chest of a living body; a potential measurer configured to perform a process of applying a current to any ones of the electrodes, and measuring potentials by means of other electrodes; an impedance acquirer, based on the applied current and the potentials obtained by the potential measurer, configured to obtain information related to an impedance of each of meshes, a chest section divided into the meshes; and an average value calculator configured to obtain a whole-region average value of impedances of all meshes of the chest section, and configured to obtain an ROI average value of impedances of meshes contained in each of ROIs, a whole region of the chest section segmented into the ROIs.

10 Claims, 3 Drawing Sheets

(56) References Cited

OTHER PUBLICATIONS

Hahn, G., et al., "Imaging pathologic pulmonary air and fluid accumulation by functional and absolute EIT," Physiol. Meas. 2006;27:S187-S198.

Wolf, G. K., et al., "Regional overdistention identified with electrical impedance tomography in the perflubron-treated lung," Physiol. Meas. 2010;31:S85-S95.

* cited by examiner

ELECTRICAL IMPEDANCE MEASURING APPARATUS

CROSS-REFERENCE TO RELATED APPLICATION(S)

This application is based upon and claims the benefit of priority from prior Japanese patent application No. 2014-037525, filed on Feb. 27, 2014, the entire contents of which are incorporated herein by reference.

BACKGROUND

The presently disclosed subject matter relates to an electrical impedance measuring apparatus which is called the EIT (Electrical Impedance Tomography) or the like.

In artificial ventilation therapy of respiratory disease such as ARDS (Acute Respiratory Distress Syndrome), a diagnosis is performed based on EIT images. In the EIT, the impedance distribution of the chest is continuously measured as a tomographic image by a chest impedance measurement.

There is a related-art technique in which, in the EIT, the lung region in a tomographic image is segmented into several ROIs (Regions of Interest), and the ratio of the value of an impedance integration of an ROI to that of the whole region is displayed in the form of a waveform or a numerical value (see U.S. Pat. No. 8,321,007).

The EIT images show the aerated state of the lungs. When aeration which is locally abnormally large is observed, there is a possibility that pulmonary alveoli are hyperextended. By contrast, when aeration which is locally abnormally small is observed, there is a possibility that pulmonary alveoli are collapsed. In treatment of ARDS or the like, it is important to know the hyperextended and collapsed states. However, the ratio of the value of an impedance integration of an ROI to that of the whole region which is obtained in the manner disclosed in U.S. Pat. No. 8,321,007 is a parameter from which the hyperextended and collapsed states are hardly known. Therefore, it is requested to obtain a parameter from which the hyperextended and collapsed states can be adequately known.

SUMMARY

The presently disclosed subject matter may provide an electrical impedance measuring apparatus having a configuration in which the hyperextended and collapsed states can be adequately known.

The electrical impedance measuring apparatus may comprise: a plurality of electrodes which are adapted to be adhered to a periphery of a chest of a living body; a potential measurer which is configured to perform a process of applying a current to any ones of the electrodes, and measuring potentials by means of other electrodes, on all of the electrodes while changing the electrodes to which the current is to be applied; an impedance acquirer which, based on the applied current and the potentials obtained by the potential measurer, is configured to obtain information related to an impedance of each of meshes, a chest section divided into the meshes; and an average value calculator which is configured to obtain a whole-region average value of impedances of all meshes of the chest section, and which is configured to obtain an ROI average value of impedances of meshes contained in each of ROIs, a whole region of the chest section segmented into the ROIs.

The electrical impedance measuring apparatus may further comprise: a display controller which is configured to cause waveforms of the whole-region average value and the ROI average value to be displayed on a display.

The display controller may produce comparison information in which the whole-region average value is compared with the ROI average value, and cause the comparison information to be displayed on the display.

The display controller may produce a numerical value which is obtained by dividing the ROI average value by the whole-region average value, or which is obtained by subtracting the whole-region average value from the ROI average value, as the comparison information, and cause the numerical value to be displayed.

The display controller may produce a graph of a numerical value which is calculated from the whole-region average value and the ROI average value, as the comparison information, and cause the graph to be displayed.

The display controller may cause the comparison information to be displayed in a trend format.

DETAILED DESCRIPTION OF EXEMPLARY EMBODIMENTS

Figure 1:
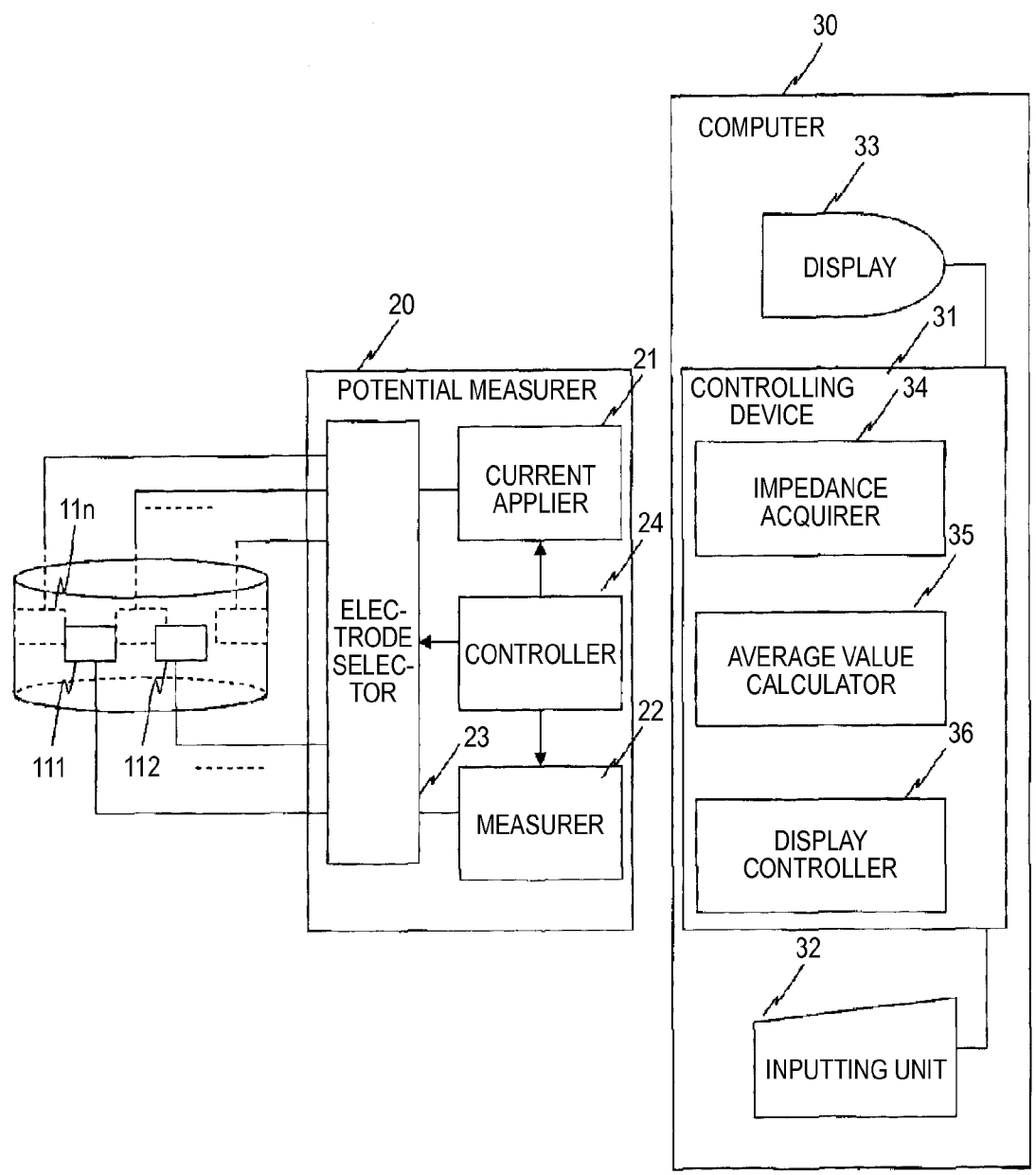
FIG. 1 is a diagram of an embodiment of the electrical impedance measuring apparatus of the presently disclosed subject matter.

Hereinafter, an embodiment of the electrical impedance measuring apparatus of the presently disclosed subject matter will be described with reference to the accompanying drawings. In the figures, the identical components are denoted by the same reference numerals, and duplicate description is omitted. FIG. 1 is a diagram of the embodiment of the electrical impedance measuring apparatus of the presently disclosed subject matter. The electrical impedance measuring apparatus mainly includes a plurality of electrodes 111 to 11$n$, a potential measurer 20, and a computer 30.

The plurality of electrodes 111 to 11$n$ are to be adhered to the periphery of the chest of the living body. For example, a necessary number of electrodes are used at the same height and at regular intervals. The potential measurer 20 includes a current applier 21, a measurer 22, an electrode selector 23, and a controller 24. Based on the control of the controller 24, the current applier 21 applies a current to electrode pairs which are connected to the current applier 21 via the electrode selector 23. The measurer 22 measures potentials produced in the electrode pairs, based on the control of the controller 24.

In accordance with the control of the controller 24, the electrode selector 23 connects the first electrode pair to which the current is to be applied, to the current applier 21, and the electrode pairs which are not connected to the current applier 21, to the measurer 22, so that the potential can be measured under this state. Then, the potential measurement is performed. Next, the electrode pair which is connected to the measurer 22 is changed to another pair so that the potential can be measured. Then, the potential measurement is performed. Thereafter, the all electrode pairs other than the first electrode pair to which the current is applied are sequentially connected to the measurer 22, and subjected to the potential measurement.

In accordance with the control of the controller 24, next, the electrode selector 23 connects the second electrode pair to which the current is to be applied, to the current applier 21, and the electrode pairs which are not connected to the current applier 21, to the measurer 22, so that the potential can be measured under this state. Then, the potential measurement is performed. Thereafter, the all electrode pairs other than the second electrode pair to which the current is applied are sequentially connected to the measurer 22, and subjected to the potential measurement. Thereafter, all the electrodes 111 to 11n are similarly sequentially selected as the electrode pair to which the current is to be applied, the all electrode pairs other than the electrode pair to which the current is applied are sequentially connected to the measurer 22, and the potential measurement is performed.

The computer 30 has a controlling device 31 which functions as a calculator having a CPU and a memory, and an inputting unit 32 and a display 33 which are connected to the controlling device 31. Command and various kinds of information are input through the inputting unit 32. The display 33 displays various kinds of display information such as an EIT image, various waveforms, numerical values, and characters.

The controlling device 31 includes an impedance acquirer 34, an average value calculator 35, and a display controller 36. The impedance acquirer 34 obtains information related to the impedance of each of meshes which are obtained by dividing a chest section region into meshes, based on the applied current and the potentials obtained by the potential measurer 20. For example, the impedances of the meshes which are obtained by dividing a chest section region into meshes may be obtained by using a related-art conversion table based on the applied current and the obtained potentials. The meshes correspond to the pixels of the EIT image, respectively. An image in which each of the meshes is converted to a color corresponding to information related to the impedance can be displayed as an EIT image. It is assumed that the information related to the impedance means the impedances which are obtained as described above, and also all kinds of information related to impedances such as absolute values of impedances and variation values of impedances with respect to a reference (for example, an impedance at a certain time).

Figure 2:
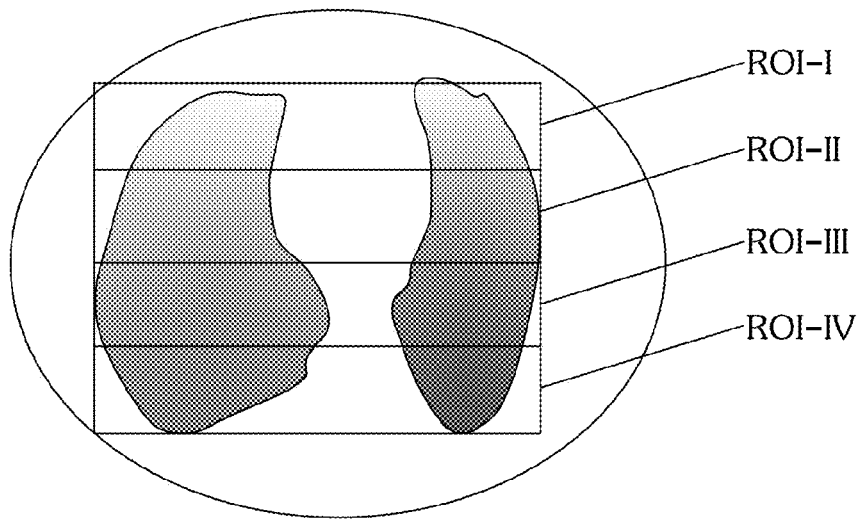
FIG. 2 is a view showing an example of ROIs which are obtained by segmenting the whole region of a chest section into four regions.

The average value calculator 35 obtains a whole-region average value of the impedances of the all meshes of the chest section, and an ROI average value of the impedances of meshes in each of ROIs which are formed by segmenting the whole region of the chest section into a plurality of regions. For example, ROI-I, ROI-II, ROI-III, and ROI-IV which are shown in FIG. 2, and which are obtained by segmenting the whole region of a chest section into four regions will be considered. Each of the ROI-I, ROI-II, ROI-III, and ROI-IV is divided into a plurality of meshes, and the impedances which are obtained by the impedance acquirer 34 are made correspond to the meshes, respectively. Therefore, the average value (whole-region average value) of the whole region of the chest section can be obtained by using the impedances. Moreover, the average values (ROI average values) of the ROI-I, ROI-II, ROI-III, and ROI-IV can be obtained by using the impedances which are made correspond to the meshes, respectively.

The display controller 36 causes the whole-region average value and ROI average values which are obtained as described above, to be displayed on the display 33. Moreover, the display controller 36 produces comparison information which is obtained by comparing the whole-region average value and ROI average values which are obtained as described above, with each other, and causes the comparison information to be displayed on the display 33. As the comparison information, numerical values which are obtained by dividing the ROI average values by the whole-region average value may be calculated, or subtracting the whole-region average value from the ROI average values, and the values may be displayed. As the comparison information, graphs of numerical values which are calculated from the whole-region average value and the ROI average values may be produced, and the graphs may be displayed. The comparison information may be displayed in time series and in a trend format.

Figure 3:
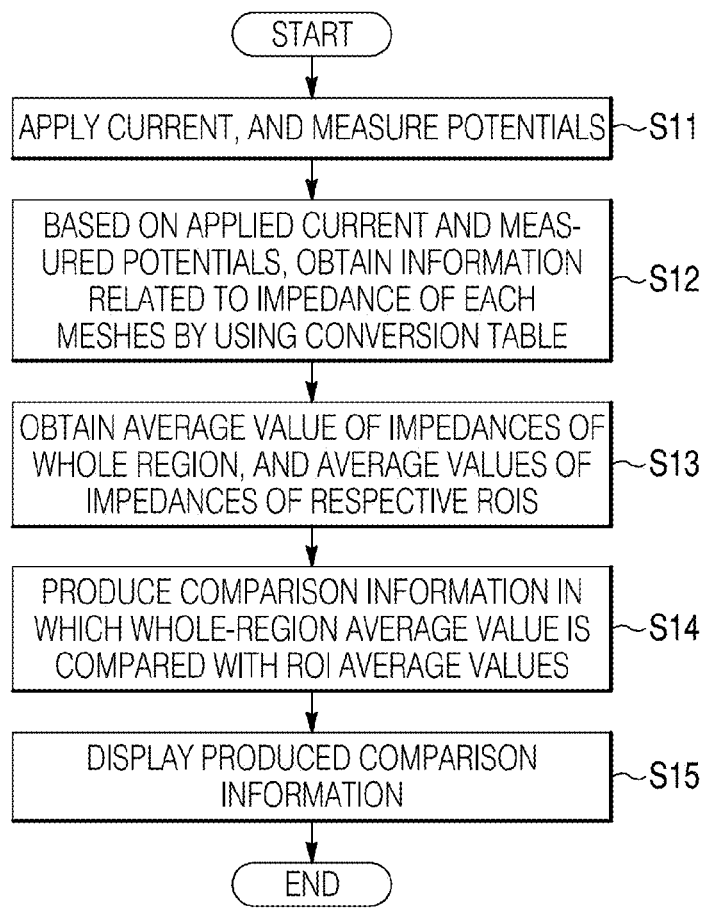
FIG. 3 is a flowchart illustrating the operation of the embodiment of the electrical impedance measuring apparatus of the presently disclosed subject matter.

The thus configured electrical impedance measuring apparatus operates as shown in the flowchart shown in, for example, FIG. 3. The operation will be described. First, the plurality of electrodes 111 to 11n are adhered to the periphery of the chest of the living body, and the measurement is started. An electrode pair is selected, and a current is applied to the selected electrode pair. The potential is obtained from an electrode pair to which the current is not applied. The potentials are measured while sequentially changing electrodes from which the potential is to be obtained. When the potential measurement is completed with respect to the all electrode pairs to which the current is not applied, the electrode pair to which the current is to be applied is changed to another electrode pair, and the subsequent potential measurement will be performed in a similar manner. In this way, the measurement is continued until the current apply is performed on the all electrode pairs, and the corresponding potential measurement is completed. Then, the series of potential measurements is ended (S11).

Based on the applied current and the measured potentials, next, the impedance of each of meshes is obtained by using the related-art conversion table (S12). By using the impedances of the meshes, moreover, the whole-region average value which is the average value of the impedances of the whole region, and the ROI average values which are the average values of the impedances of the respective ROIs are obtained (S13). Next, the comparison information which is obtained by comparing the whole-region average value with the ROI average values is produced (S14), and the produced comparison information is displayed (S15).

Figure 4:
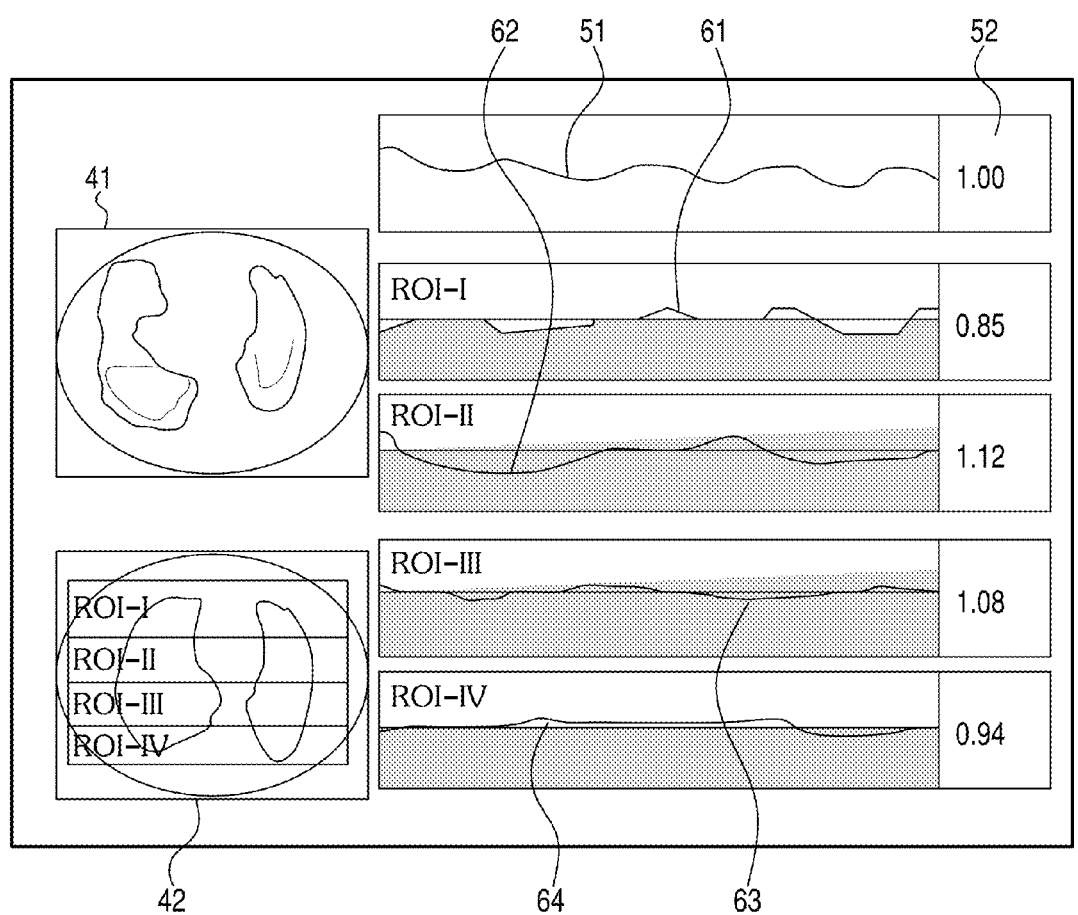
FIG. 4 is a view showing an example of display of comparison information by the embodiment of the electrical impedance measuring apparatus of the presently disclosed subject matter.

For example, the produced information and the like are displayed as the image shown in FIG. 4. For example, an electrical impedance image (EIT image) 41 having a size which is about one-twelfth of one screen is displayed in an upper left area of the one screen, and, below the image, an image 42 indicating the ROIs is displayed in the same size as the EIT image 41. In the image 42 indicating the ROIs, it is possible to clearly indicate the places where the ROI-I, ROI-II, ROI-III, and ROI-IV which are obtained by segmenting the whole region of into four regions are located.

In the area on the right side of the EIT image 41, a waveform 51 of the average value of the impedances of the whole region is displayed in a trend format with a length which is about a half of the lateral width of the screen. Numerical data 52 are displayed on the right side of the waveform. Comparison information waveforms 61 to 64 of the four segmented ROI-I, ROI-II, ROI-III, and ROI-IV are displayed below the waveform 51. Each of the comparison information waveforms 61 to 64 is a waveform of the average value of the impedances of the corresponding one of the four segmented ROI-I, ROI-II, ROI-III, and ROI-IV. The waveforms are displayed on the same time axis as that of the waveform 51. In the area on the right side of each of the comparison information waveforms 61 to 64, a value which is obtained by dividing the average value of the impedances of the corresponding one of the four segmented ROI-I, ROI-II, ROI-III, and ROI-IV by that of the whole region is displayed as a numerical value.

As described above, comparison information is displayed on the display. Therefore, it is easy to know whether the average impedances of a plurality of regions which are obtained by segmenting a chest section into a plurality of regions are prominently larger than the impedance of the whole region or not. In the case of an extreme prominence, it is possible to visually determine that hyperextension or collapse occurs.

The average values of the impedances of the four segmented ROI-I, ROI-II, ROI-III, and ROI-IV, and the values which are obtained by dividing the average value of the impedances by that of the whole region are used as comparison information. The number of segments may be smaller or larger than four. In addition to the quotients, comparison results such as subtraction results may be used as comparison information. In place of the segmenting method in which line segments that extend from one side of the body to the other side are used as shown in FIG. 2, a method in which line segments that extend from the front side of the body to the back side are used may be employed. Alternatively, ROIs may be produced by combinedly using these lines.

According to the electrical impedance measuring apparatus of the presently disclosed subject matter, the whole-region average value of the impedances of all meshes of a chest section is obtained, and the ROI average value of the impedances of meshes in each of ROIs which are formed by segmenting the chest section into a plurality of regions is obtained. Therefore, it is easy to know whether the average impedances of the plurality of regions which are obtained by segmenting a chest section are prominently larger than the impedance of the whole region or not. In the case of an extreme prominence, it is possible to suspect that hyperextension or collapse may occur. Consequently, the hyperextended and collapsed states can be adequately known.

What is claimed is:

1. An electrical impedance measuring apparatus comprising:
   a plurality of electrodes which are adapted to be adhered to a periphery of a chest of a living body;
   a potential measurer having a controller and which is configured to perform a process of applying a current to any of the electrodes, and measuring potentials by means of other electrodes, on all of the electrodes while changing the electrodes to which the current is to be applied; and
   a computer having a processor and memory, and being configured to:
      based on the applied current and the potentials obtained by the potential measurer, obtain information related to an impedance of each of a plurality of meshes, a chest section being divided into the meshes;
      obtain a whole-region average value of impedances of all meshes of the chest section, and which is configured to obtain a region of interest (ROI) average value of impedances of meshes contained in each of a plurality of ROIs, a whole region of the chest section being segmented into the ROIs; and
      cause waveforms of the whole-region average value and the ROI average value to be displayed on a same time axis on a display.

2. The electrical impedance measuring apparatus according to claim 1, wherein the computer is further configured to produce comparison information in which the whole-region average value is compared with the ROI average value, and cause the comparison information to be displayed on the display.

3. The electrical impedance measuring apparatus according to claim 1, wherein the computer is further configured to produce a numerical value which is obtained by dividing the ROI average value by the whole-region average value, or which is obtained by subtracting the whole-region average value from the ROI average value, and cause the numerical value to be displayed.

4. The electrical impedance measuring apparatus according to claim 1, wherein the computer is further configured to produce a graph of a numerical value which is calculated from the whole-region average value and the ROI average value, and cause the graph to be displayed.

5. The electrical impedance measuring apparatus according to claim 2, wherein the computer is further configured to cause the comparison information to be displayed in a trend format.

6. An electrical impedance measuring method comprising:
   applying a current to any of a plurality of electrodes adapted to be adhered to a periphery of a chest of a living body;
   measuring potentials by means of other electrodes, on all of the electrodes while changing the electrodes to which the current is applied;
   obtaining information related to an impedance of each of a plurality of meshes based on the applied current and the measured potentials, a chest section being divided into the meshes;
   obtaining a whole-region average value of impedances of all meshes of the chest section;
   obtaining a region of interest (ROI) average value of impedances of meshes contained in each of a plurality of ROIs, a whole region of the chest section being segmented into the ROIs; and
   displaying waveforms of the whole-region average value and the ROI average value on a same time axis.

7. The electrical impedance measuring method according to claim 6, further comprising:
   producing comparison information in which the whole-region average value is compared with the ROI average value; and
   displaying the comparison information.

8. The electrical impedance measuring method according to claim 6, further comprising:
   producing a numerical value which is obtained by dividing the ROI average value by the whole-region average value, or which is obtained by subtracting the whole-region average value from the ROI average value; and
   displaying the numerical value.

9. The electrical impedance measuring method according to claim 6, further comprising:
   producing a graph of a numerical value which is calculated from the whole-region average value and the ROI average value; and
   displaying the graph.

10. The electrical impedance measuring method according to claim 7, wherein the display controller causes the comparison information to be displayed in a trend format.

\* \* \* \* \*